(12) United States Patent
Gross

(10) Patent No.: US 8,287,902 B2
(45) Date of Patent: Oct. 16, 2012

(54) ENHANCED-DIFFUSION CAPSULE

(75) Inventor: Yossi Gross, Moshav Mazor (IL)

(73) Assignee: Rainbow Medical Ltd., Herzliya (IL)

( * ) Notice: Subject to any disclaimer, the term of this patent is extended or adjusted under 35 U.S.C. 154(b) by 339 days.

(21) Appl. No.: 12/508,086

(22) Filed: Jul. 23, 2009

(65) Prior Publication Data

US 2010/0021536 A1    Jan. 28, 2010

Related U.S. Application Data

(60) Provisional application No. 61/135,807, filed on Jul. 23, 2008.

(51) Int. Cl.
  *A61K 9/48*      (2006.01)
  *A61N 1/30*      (2006.01)
  *A61N 1/00*      (2006.01)
  *A61M 1/00*      (2006.01)
  *A61M 3/00*      (2006.01)

(52) U.S. Cl. .......... 424/451; 424/452; 424/463; 604/19; 604/27; 604/31; 604/43; 607/154

(58) Field of Classification Search .................. 424/451, 424/452, 463; 604/19, 27, 31, 43; 607/154
See application file for complete search history.

(56) References Cited

U.S. PATENT DOCUMENTS

| | | | |
|---|---|---|---|
| 5,002,772 A * | 3/1991 | Curatolo et al. ............. 424/438 |
| 5,443,843 A * | 8/1995 | Curatolo et al. ............. 424/464 |
| 5,443,846 A * | 8/1995 | Yoshioka et al. ............. 424/498 |
| 6,235,313 B1 | 5/2001 | Mathiowitz et al. |
| 6,245,057 B1 * | 6/2001 | Sieben et al. ............. 604/891.1 |
| 6,685,962 B2 | 2/2004 | Friedman et al. |
| 6,958,034 B2 | 10/2005 | Iddan |
| 7,009,634 B2 | 3/2006 | Iddan et al. |
| 7,160,258 B2 | 1/2007 | Imran et al. |
| 2003/0153866 A1 | 8/2003 | Long et al. |
| 2004/0050394 A1 | 3/2004 | Jin |
| 2004/0180086 A1 | 9/2004 | Ramtoola et al. |

(Continued)

FOREIGN PATENT DOCUMENTS

WO    2005105053 A2    11/2005

(Continued)

OTHER PUBLICATIONS

Sarah L. Tao, et al., "Gastrointestinal patch systems for oral drug delivery", DDT vol. 10, No. 13, pp. 909-915, Jul. 2005.

(Continued)

*Primary Examiner* — Johann Richter
*Assistant Examiner* — Jane C Osewcki
(74) *Attorney, Agent, or Firm* — Sughrue Mion, PLLC

(57) ABSTRACT

An ingestible capsule is provided for delivering medication to a subject. A capsule coating dissolves in a gastrointestinal tract of the subject. An inner core of the capsule has an outer surface associated therewith. The outer surface is disposed within the coating and expands when the coating dissolves. A medication is disposed on the outer surface, and the outer surface is configured such that the medication contacts an intestinal wall of the subject when the outer surface expands. Other embodiments are also provided.

26 Claims, 7 Drawing Sheets

U.S. PATENT DOCUMENTS

| | | |
|---|---|---|
| 2004/0253304 A1 | 12/2004 | Gross et al. |
| 2004/0267240 A1 | 12/2004 | Gross et al. |
| 2005/0058701 A1 | 3/2005 | Gross et al. |
| 2006/0178557 A1 | 8/2006 | Mintchev et al. |
| 2006/0276844 A1 | 12/2006 | Alon et al. |
| 2008/0063703 A1 | 3/2008 | Gross et al. |
| 2008/0188837 A1 | 8/2008 | Belsky et al. |
| 2008/0275430 A1 | 11/2008 | Belsky et al. |

FOREIGN PATENT DOCUMENTS

| | | |
|---|---|---|
| WO | WO2007/086078 A2 * | 8/2007 |
| WO | WO2007086078 A2 * | 8/2007 |

OTHER PUBLICATIONS

Klausner et al., "Expandable Gastroretentive Dosage Forms", Journal of Controlled Release 90 (2003) 143-162.

* cited by examiner

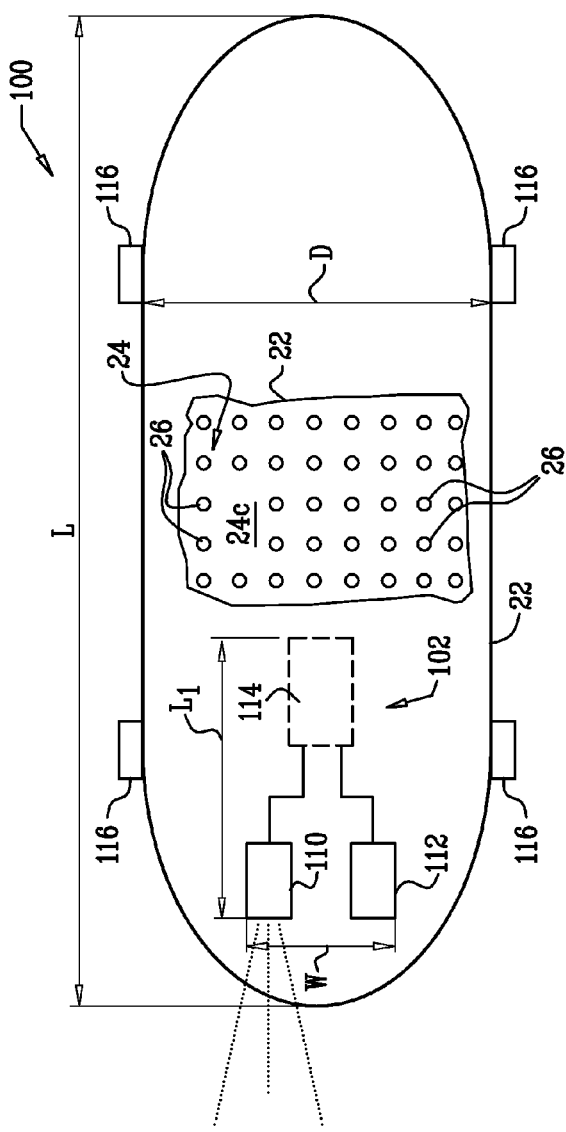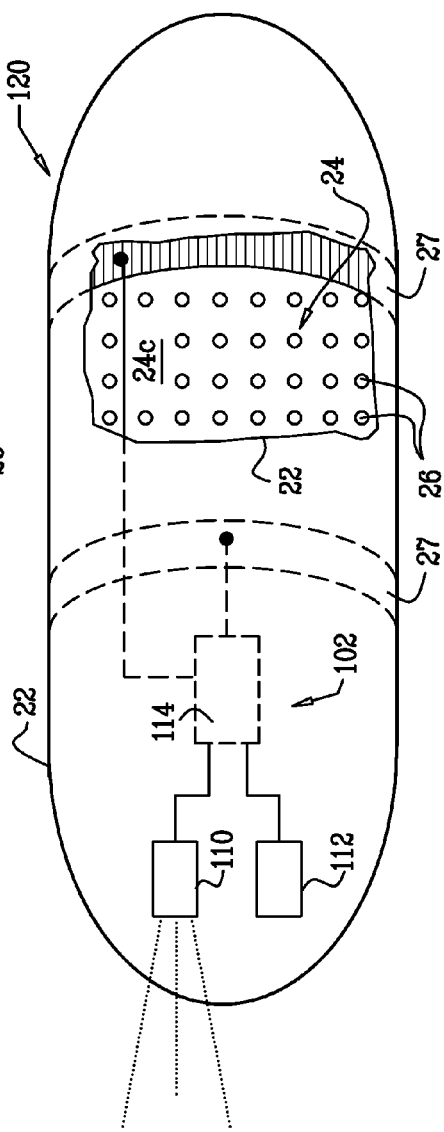

ENHANCED-DIFFUSION CAPSULE

CROSS-REFERENCES TO RELATED APPLICATIONS

This application claims the benefit of U.S. Provisional Patent Application 61/135,807 to Gross, entitled "Enhanced-diffusion capsule," filed Jul. 23, 2008, which is incorporated herein by reference.

FIELD OF THE INVENTION

The present invention generally relates to medical apparatus. Specifically, the present invention relates to an ingestible capsule for administering medication to a subject.

BACKGROUND OF THE INVENTION

Medication is frequently stored in a capsule and administered to a subject who swallows the capsule. The medication passes through the intestinal wall and enters the blood of the subject.

US Patent Application Publication 2004/0253304 to Gross et al., which is incorporated herein by reference, describes apparatus for drug administration, including an ingestible capsule. The capsule includes a drug, stored by the capsule. An environmentally-sensitive mechanism is adapted to change a state thereof responsive to a disposition of the capsule within a gastrointestinal tract of a subject. The Gross et al. publication describes a driving mechanism, that in response to a change of state of the environmentally-sensitive mechanism, is adapted to drive the drug directly through an endothelial or an epithelial layer of the gastrointestinal tract.

US Patent Application Publication 2004/0267240 to Gross et al., which is incorporated herein by reference, describes apparatus for drug administration, including an ingestible capsule, which includes a drug, stored by the capsule, and an environmentally-sensitive mechanism, adapted to change a state thereof responsively to a disposition of the capsule within a gastrointestinal (GI) tract of a subject. The capsule further includes first and second electrodes, and a control component, adapted to facilitate passage of the drug, in response to a change of state of the environmentally-sensitive mechanism, through an epithelial layer of the GI tract by driving the first and second electrodes to apply a "low intensity time-varying" (LITV) signal.

US Patent Application Publication 2005/0058701 to Gross et al., which is incorporated herein by reference, describes apparatus for drug administration, including an ingestible capsule, which includes a drug, stored by the capsule, and an environmentally-sensitive mechanism, adapted to change a state thereof responsively to a disposition of the capsule within a gastrointestinal (GI) tract of a subject. The capsule further includes first and second electrodes, and a control component, adapted to facilitate passage of the drug, in response to a change of state of the environmentally-sensitive mechanism, through an epithelial layer of the GI tract, by driving the first and second electrodes to apply a series of pulses at a current of less than about 5 mA, at a frequency of between about 12 Hz and about 24 Hz, and with a pulse duration of between about 0.5 milliseconds and about 3 milliseconds.

US Patent Application Publication 2006/0178557 to Mintchev et al. describes a method and apparatus for permitting capsule imaging of organs having larger lumens without tumbling, and includes an outer shell surrounding the capsule that targets the colon, as an example. Once the colon has been reached, the shell breaks or dissolves, and allows expansion of expandable materials attached to each end of the capsule, thereby stabilizing the capsule in the targeted organ, while permitting it to be moved by peristalsis and/or other means for locating the capsule. Imagers and light emitting diodes (LEDs) are activated during the expansion process, and enable overlapping of images. The capsule is moved through the colon, taking images at chosen frame rates with data being wirelessly transmitted by means of an RF transmitter, and is eventually expelled from the body.

U.S. Pat. No. 7,009,634 to Iddan describes a system and method for obtaining in vivo images. The system contains an imaging system and an ultra low power radio frequency transmitter for transmitting signals from the complementary metal oxide semiconductor (CMOS) imaging camera to a receiving system located outside a patient. The imaging system includes at least one CMOS imaging camera, at least one illumination source for illuminating an in vivo site, and an optical system for imaging the in vivo site onto the CMOS imaging camera.

U.S. Pat. No. 6,235,313 to Mathiowitz et al. describes bioadhesive polymers in the form of, or as a coating on, microcapsules containing drugs or bioactive substances which may serve for therapeutic, or diagnostic purposes in diseases of the gastrointestinal tract. The polymeric microspheres are all described as having a bioadhesive force of at least 11 mN/cm.sup.2 (110 N/m.sup.2). Techniques for the fabrication of bioadhesive microspheres, as well as a method for measuring bioadhesive forces between microspheres and selected segments of the gastrointestinal tract in vitro are also described. This quantitative method is described as providing a means to establish a correlation between the chemical nature, the surface morphology and the dimensions of drug-loaded microspheres on one hand and bioadhesive forces on the other, allowing the screening of the most promising materials from a relatively large group of natural and synthetic polymers which, from theoretical considerations, should be used for making bioadhesive microspheres.

US Patent Application Publication 2004/0180086 to Ramtoola describes gastro-retentive dosage forms for prolonged delivery of levodopa and carbidopalevodopa combinations. The dosage forms comprise a tablet containing the active ingredient and a gas-generating agent sealed within an expandable, hydrophilic, water-permeable and substantially gas-impermeable membrane. Upon contact with gastric fluid, the membrane expands as a result of the release of gas from the gas-generating agent in the tablet. The expanded membrane is described as being retained in the stomach for a prolonged period of time, up to 24 hours or more, during which period the active ingredient is released from the tablet providing delivery of levodopa to the site of optimum absorption in the upper small intestine.

An article entitled "Gastrointestinal patch systems for oral drug delivery" by Tao et al. provides a review of gastrointestinal patch systems with integrated multifunctions. Several gastrointestinal patch systems are described as providing bioadhesion, drug protection and unidirectional release. This combination of function is described as improving the overall oral bioavailability of large molecules that can currently be delivered only by injection, for example, epoetin-alpha and granulocyte-colony-stimulating factor, which are commonly used to treat chemotherapy-associated anemia and leukopenia, respectively. Furthermore, self-regulated release and cell-specific targeting are described as providing additional "smart" characteristics to this innovative therapeutic platform.

The following references may be of interest:

PCT Publication WO 05/105053 to Gross et al.

U.S. Pat. No. 6,958,034 to Iddan

U.S. Pat. No. 6,685,962 to Friedman et al.

U.S. Pat. No. 7,160,258 to Imran et al.

US Patent Application Publication 2004/0050394 to Jin

US Patent Application Publication 2006/0276844 to Alon et al.

US Patent Application Publication 2008/0063703 to Gross et al.

US Patent Application Publication 2008/0275430 to Belsky et al.

US Patent Application Publication 2008/0188837 to Belsky et al.

US Patent Application Publication 2003/0153866 to Long et al.

"Expandable gastroretentive dosage forms," by Klausner et al., Journal of Controlled Release 90 (2003) 143-162

SUMMARY OF THE INVENTION

In some embodiments of the present invention, a subject is administered medication in the form of an ingestible capsule. In some embodiments, the capsule comprises an inner core having an outer surface, the outer surface being disposed within a coating, for example an enteric coating and/or a gel. The medication is disposed on the outer surface of the inner core. The coating of the capsule dissolves when the capsule reaches the small intestine, enabling the outer surface of the inner core to expand within the small intestine. For example, the outer surface of the inner core may stretch or unfold in response to contact of the inner core or the outer surface with fluid in the small intestine, or in response to no longer being constrained by the enteric coating or gel. The outer surface expands and establishes contact with the wall of the intestine. As a consequence of this expansion, the medication disposed on the outer surface of the inner core contacts the intestinal wall. Alternatively, the outer surface is large enough to establish contact with the intestinal wall even without expanding. Regardless of whether the outer surface is configured to expand in the small intestine, the medication is typically disposed on the outer surface in a high concentration. For example, a medication layer on the outer surface may contain more than 90% by volume of the active medication. The quantity of the medication delivered to the subject is high because (a) the concentration of the drug that is disposed on the outer surface is high, (b) good contact is made between the outer surface and the intestinal wall, and (c) diffusion of the medication in the medication layer through the subject's intestinal wall is enhanced by the combination of (a) and (b).

In some embodiments, establishing contact between the medication and the wall of the intestine allows oral administration of large molecules which generally have low availability via oral delivery when contact between the medication and the wall of the intestine is not established. In some embodiments, techniques for establishing contact between a high concentration of a medication and the intestinal wall, as described hereinbelow, are used in combination with techniques for increasing delivery of a medication through the intestinal wall by driving a current into the intestinal wall. For example, the techniques described hereinbelow may be used in combination with the patent applications to Gross, which are incorporated by reference herein.

Typically, the medication is in powder or gel form, and diffuses rapidly through the wall of the small intestine in response to the high concentration of the medication and the complete or nearly complete contact with the intestinal wall of the expanded outer surface of the inner core.

In some embodiments, the capsule comprises an adhesive agent, which holds the expanded outer surface in position during delivery of the medication through the intestinal wall. Alternatively or additionally, the delivery of the medication through the intestinal wall is enhanced by incorporating a chemical or other type of enhancer in the capsule.

In some embodiments, a control unit is disposed within the inner core. Typically, the outer surface is coupled to at least one electrode. In some embodiments, the electrode constitutes the outer surface of the inner core, or a part thereof. The control unit drives a current through the electrode into the intestinal wall. In one embodiment, the control unit iontophoretically drives the medication disposed on the outer surface through the wall of the intestine. Alternatively or additionally, the control unit drives a current configured to increase the permeability of the intestinal wall to the medication.

In some embodiments, a capsule is administered to the subject, the capsule having a lateral surface that is sized such that medication disposed on the lateral surface contacts the subject's intestinal wall when the capsule is within the subject's gastrointestinal tract. For example, the lateral surface may define a lateral diameter thereof of at least 8 mm (the length of the capsule perpendicular to the lateral diameter being at least 8 mm). In some embodiments, a device, such as an imaging device, is disposed within the capsule.

In some embodiments, when the capsule is disposed within the subject's gastrointestinal tract, the capsule allows gastrointestinal contents to pass into the capsule, from the end of the capsule which is disposed proximally with respect to the gastrointestinal tract, then through the body of the capsule, and then out of the capsule from the end of the capsule which is disposed distally. For example, at least a portion of the capsule surface at each end of the capsule may be biodegradable. Alternatively, at least a portion of each of the two ends of the capsule may be open when the capsule is administered to the subject. For example, the capsule may be tube-shaped when swallowed.

There is therefore provided, in accordance with an embodiment of the invention, an ingestible capsule for delivering medication to a subject, including:

a coating configured to dissolve in a gastrointestinal tract of the subject;

an inner core having an outer surface associated therewith, the outer surface being disposed within the coating and configured to expand when the coating dissolves; and a medication disposed on the outer surface, the outer surface being configured such that the medication contacts an intestinal wall of the subject when the outer surface expands.

In an embodiment, the capsule further includes an adhesive agent configured to adhere the medication to the subject's intestinal wall during delivery of the medication.

In an embodiment, the medication includes a powder.

In an embodiment, the medication includes a gel.

In an embodiment, the outer surface has a plurality of arms extending outward radially, prior to expansion.

In an embodiment, the outer surface has a star-shaped cross-section prior to expansion.

In an embodiment, the outer surface is generally circular in cross-section prior to expansion.

In an embodiment, the outer surface is generally circular in cross-section following expansion.

In an embodiment, the outer surface is configured such that on expansion of the outer surface, the medication disposed on the outer surface contacts the intestinal wall providing substantially 360 degrees of contact of the medication with the intestinal wall.

In an embodiment, the coating includes an enteric coating.

In an embodiment, the coating includes a gelatin coating.

In an embodiment, the gelatin coating is configured to constrain the outer surface from expanding before the gelatin coating dissolves.

In an embodiment, the capsule further includes a chemical enhancer configured to enhance delivery of the medication to the subject.

In an embodiment, the chemical enhancer includes lipophilic molecules configured to enhance diffusion of the medication through an epithelial layer of the subject's intestinal wall.

In an embodiment, a mean depth of the medication on the outer surface is less than 2 mm.

In an embodiment, the mean depth is less than 1.5 mm.

In an embodiment, a diameter of the inner core after expansion is between 8 mm and 20 mm.

In an embodiment, the diameter of the inner core after expansion is between 10 mm and 14 mm.

In an embodiment, the outer surface is configured to facilitate delivery of the medication through the intestinal wall by establishing the contact between the medication and the intestinal wall.

In an embodiment, the capsule further includes an adhesive agent configured to hold the expanded outer surface in position during the delivery of the medication through the intestinal wall.

In an embodiment, the outer surface associated with the inner core constitutes the outer surface of the inner core.

In an embodiment, the inner core includes a material configured to expand by absorbing liquid.

In an embodiment, the material includes a polymer.

In an embodiment, the capsule further includes a control unit and two electrodes, wherein the control unit is configured to facilitate delivery of the medication through the intestinal wall by driving a current through the electrodes.

In an embodiment, the control unit is configured to facilitate delivery of the medication through the intestinal wall by iontophoretically driving the medication through the intestinal wall.

In an embodiment, the control unit is configured to facilitate delivery of the medication through the intestinal wall by configuring the current to increase permeability of the intestinal wall to the medication.

In an embodiment, at least one of the electrodes includes a foil electrode surrounding the inner core.

In an embodiment, the foil electrode forms at least a portion of the outer surface.

In an embodiment, the medication is disposed on the foil electrode.

In an embodiment, the outer surface is configured to be separated at least in part from the inner core during the expansion of the outer surface.

In an embodiment, the outer surface includes one or more flaps wrapped around the inner core prior to expansion, which are configured to separate from the inner core by unrolling from the inner core.

In an embodiment, the one or more flaps include a single flap that is wrapped around the inner core.

In an embodiment, the one or more flaps include a plurality of flaps.

In an embodiment, the capsule is configured to allow gastrointestinal contents of the subject to pass through the capsule, from one end of the capsule to another end of the capsule, when the capsule is disposed within the subject's gastrointestinal tract and subsequent to expansion.

In an embodiment, the capsule is shaped to define two ends thereof and a capsule end-surface at each end of the capsule, at least a portion of each of the capsule end-surfaces being biodegradable.

In an embodiment, at least a portion of the inner core is configured to biodegrade when the capsule is disposed within the subject's gastrointestinal tract.

In an embodiment, the inner core defines a lumen therethrough.

In an embodiment, the capsule is shaped to define two ends thereof, and at least a portion of each end of the capsule is open, allowing passage of the subject's gastrointestinal contents through the capsule.

In an embodiment, the open portion of each of the ends of the capsule is shaped to define a characteristic diameter thereof having a diameter at least 50% of a diameter of the capsule, when the capsule is expanded.

There is additionally provided, in accordance with an embodiment of the present invention a method, including:
administering a capsule to a subject; and
establishing contact between (a) a wall of an intestine of the subject and (b) a medication disposed on a surface disposed within the capsule, by expanding the surface in a gastrointestinal tract of the subject.

There is additionally provided, in accordance with an embodiment of the present invention, an ingestible capsule for delivering medication to a subject, including:
a surface, defining a lateral diameter thereof of being at least 8 mm, a length of the capsule, perpendicular to the lateral diameter, being at least 8 mm; and
a medication disposed on the surface, at least 80% of the medication being within 1 mm of an outermost border of the capsule.

In an embodiment, the lateral diameter is 20 mm to 25 mm.

In an embodiment, the surface is sized such that it holds the surface in position in a gastrointestinal tract of the subject during delivery of the medication through a wall of an intestine of the subject.

In an embodiment, the capsule further includes an adhesive agent configured to adhere the medication to a wall of an intestine of the subject during delivery of the medication.

In an embodiment, the capsule further includes an adhesive agent configured to adhere the surface in position during delivery of the medication.

In an embodiment, at least 90% of the medication is within an outer 1 mm of the radius of the capsule.

In an embodiment, the lateral diameter is 10 mm to 20 mm.

In an embodiment, the lateral diameter is 12 mm to 15 mm.

In an embodiment, the capsule further includes a chemical enhancer configured to enhance delivery of the medication to the subject.

In an embodiment, the chemical enhancer includes lipophilic molecules configured to enhance diffusion of the medication through an epithelial layer of a gastrointestinal tract of the subject.

In an embodiment, the capsule further includes a control unit and two electrodes, and the control unit is configured to facilitate delivery of the medication by driving a current through the electrodes.

In an embodiment, the control unit is configured to facilitate delivery of the medication by iontophoretically driving the medication.

In an embodiment, the control unit is configured to facilitate delivery of the medication through an intestinal wall by configuring the current to increase permeability of the intestinal wall to the medication.

In an embodiment, at least one of the electrodes includes a foil electrode surrounding the surface.

In an embodiment, at least one of the electrodes includes a foil electrode that forms at least a portion of the surface.

In an embodiment, at least one of the electrodes includes a foil electrode, and the medication is disposed on the foil electrode.

In an embodiment, the capsule further includes a device disposed within the capsule.

In an embodiment, a length of the device is greater than 3 mm and wherein a width of the device is greater than 3 mm.

In an embodiment, the device includes a sensor configured to detect a parameter while the sensor is disposed within a gastrointestinal tract of the subject.

In an embodiment, the capsule is configured to facilitate delivery of the medication through an intestinal wall of the gastrointestinal tract, in response to the parameter detected by the sensor.

In an embodiment, the device includes an imaging device configured to image a gastrointestinal tract of the subject.

In an embodiment, the capsule is configured to facilitate delivery of the medication through an intestinal wall of the gastrointestinal tract in response to an image of the subject's gastrointestinal tract imaged by the imaging device.

In an embodiment, the capsule further includes a coating configured to dissolve in a gastrointestinal tract of the subject, the surface and the medication being disposed within the coating.

In an embodiment, the coating includes an enteric coating.

In an embodiment, the coating includes a gelatin coating.

In an embodiment, the capsule is configured to allow gastrointestinal contents of the subject to pass through the capsule, from one end of the capsule to another end of the capsule, when the capsule is disposed within a gastrointestinal tract of the subject.

In an embodiment, the capsule is shaped to define two ends thereof and a capsule end-surface at each end of the capsule, at least a portion of each of the capsule end-surfaces being biodegradable.

In an embodiment, the capsule is shaped to define two ends thereof and at least a portion of each end of the capsule is open, allowing passage of the subject's gastrointestinal contents through the capsule.

In an embodiment, the open portion of each of the ends of the capsule is shaped to define a characteristic diameter thereof having a diameter at least 50% of the lateral diameter of the capsule.

There is further provided, in accordance with an embodiment of the present invention, a method, including:

identifying a subject in need of a medication; and establishing contact between (a) an intestinal wall of the subject and (b) the medication, by administering a capsule to the subject, the capsule having a surface, defining a lateral diameter thereof of at least 8 mm, a length of the capsule, perpendicular to the lateral diameter, being at least 8 mm, the medication being disposed on the surface of the capsule, the capsule being sized such that the surface of the capsule contacts the subject's intestinal wall when the capsule is disposed within a gastrointestinal tract of the subject, and at least 80% of the medication being within 1 mm of an outermost border of the capsule.

There is additionally provided, in accordance with an embodiment of the present invention, an ingestible capsule for delivering medication to a subject, including:

a coating configured to dissolve in a gastrointestinal tract of the subject;

one or more flaps rolled-up within the coating and configured to unroll when the coating dissolves; and a medication disposed on the one or more flaps, the flaps being configured such that the medication contacts an intestinal wall of the subject when the one or more flaps unroll.

There is additionally provided, in accordance with an embodiment of the present invention, an ingestible capsule for delivering medication to a subject, including:

a surface; and a medication disposed on the surface, at least 80% of the medication being within 1 mm of an outermost border of the capsule.

There is additionally provided, in accordance with an embodiment of the present invention, an ingestible capsule for delivering medication to a subject, including:

a surface; and a medication-layer including an active medication disposed on the surface, the medication-layer including more than 90% by volume of the active medication.

The present invention will be more fully understood from the following detailed description of embodiments thereof, taken together with the drawings, in which:

BRIEF DESCRIPTION OF THE DRAWINGS

FIG. 7 is a schematic illustration of a device inside an ingestible capsule, in accordance with an embodiment of the present invention;

FIG. 8 is a schematic illustration of a device inside an ingestible capsule, in accordance with another embodiment of the present invention;

DETAILED DESCRIPTION OF EMBODIMENTS

Figure 1A:
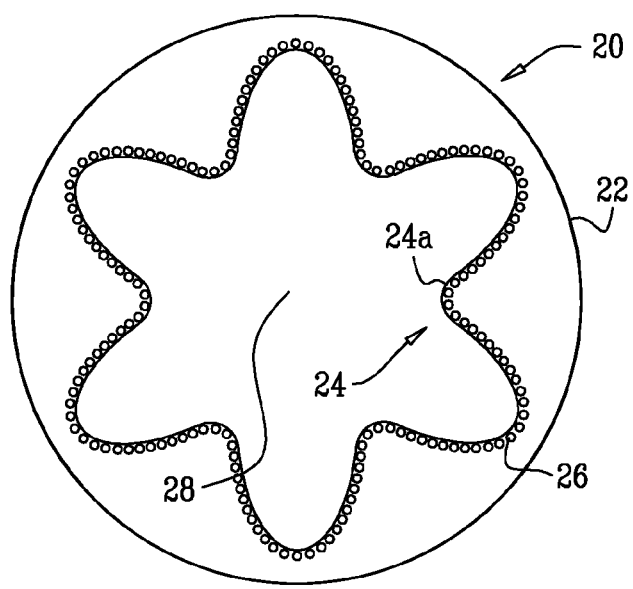
FIG. 1A is a schematic illustration of an ingestible expansible capsule, in accordance with an embodiment of the present invention.
Figure 1B:
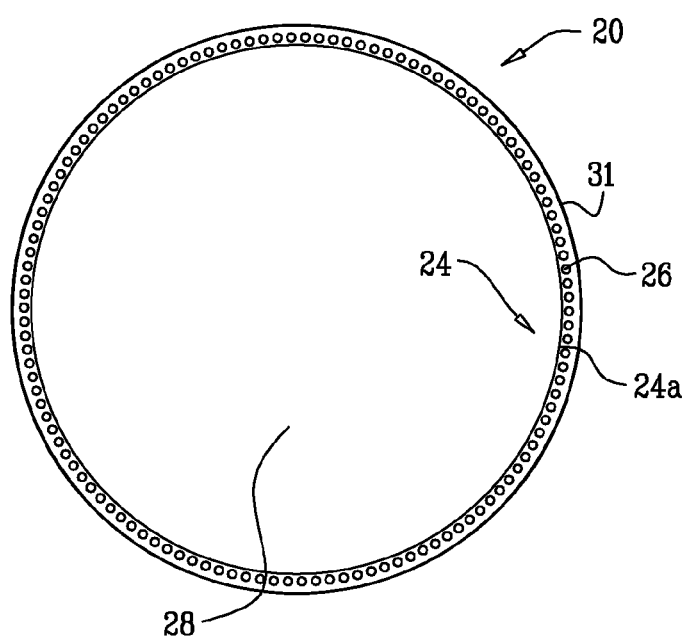
FIG. 1B is a schematic illustration of a portion of the ingestible capsule of FIG. 1A, in accordance with an embodiment of the present invention.

Reference is now made to FIGS. 1A and 1B, which are schematic illustrations of a capsule 20, configured for ingestion by a subject, in accordance with an embodiment of the present invention. Capsule 20 comprises an inner core 28 having an outer surface 24a. It is noted that throughout the Detailed Description of Embodiments, the numeral 24 is generally used to denote an outer surface, and individual outer surfaces are additionally denoted as 24a, 24b, 24c, or 24d. Outer surface 24a is disposed within a coating 22. A medication 26 is disposed on outer surface 24a of inner core 28. In some embodiments, the medication comprises a powder. In some embodiments, medication 26 can be sprayed, coated or printed on inner core 28 of capsule 20 using techniques known in the art. The mean depth of the medication on the outer surface is typically less than 2 mm, for example, less than 1.5 mm.

Coating 22 of capsule 20 comprises gelatin or another suitable material that dissolves when capsule 20 reaches the small intestine, using techniques which are known in the art. In some embodiments, before coating 22 dissolves, the coating constrains outer surface 24a, preventing it from expanding. Outer surface 24a of inner core 28 is thereby able to expand within the small intestine, for example by absorbing liquid, or by expanding a gas in a chamber surrounded by the outer surface. Prior to expansion, outer surface 24a is star-shaped, as shown in FIG. 1A, or, alternatively, the outer surface has a different shape (e.g., as described elsewhere hereinbelow). Following expansion, as shown in FIG. 1B, outer surface 24a is generally circular, because it is constrained by contact with the wall of the small intestine 31, and/or because the outer surface is inherently circular, and is constrained within the capsule to be star-shaped. Typically, inner core 28 can expand such that its diameter is between 8 mm and 20 mm, for example between 10 mm and 14 mm or between 12 and 15 mm. In some embodiments, when it is expanded, inner core 28 has a diameter that is similar to that of capsule 100, described hereinbelow with respect to FIG. 7.

Outer surface 24a expands by stretching and/or unfolding in response to contact of the inner core or the outer surface with fluid in the small intestine, or in response to no longer being constrained by the enteric coating. Once expanded, outer surface 24a establishes contact with the wall of small intestine 31, as shown in FIG. 1B. As a consequence of this expansion, the medication disposed on outer surface 24a typically has substantially 360 degrees of contact with intestinal wall 31. Alternatively, if the medication is only disposed on a smaller portion of the outer surface, then the contact area is correspondingly reduced. In some embodiments, capsule 20 comprises an adhesive agent, which holds expanded outer surface 24a in position during delivery of the medication through the wall of the intestine. Alternatively or additionally, the delivery of the medication through the intestinal wall is enhanced by incorporating a chemical enhancer in the capsule, e.g., by incorporating the chemical enhancer into medication 26. For example, lipophilic molecules may be incorporated into the capsule, the lipophilic molecules enhancing diffusion of the medication across the epithelial layer of the subject's gastrointestinal tract.

Following delivery of medication 26, inner core 28 is passed from the body. In one embodiment, inner core 28 comprises a biodegradable substance, which biodegrades to facilitate its separation from the wall of the intestine following delivery of the drug. Alternatively or additionally, inner core 28 comprises a polymer that absorbs water, expands in the small intestine, and is subsequently broken down by bacteria and/or by the pH found in the colon. In this manner, the inner core, which had been substantially enlarged to facilitate drug delivery, decreases in size or otherwise is enabled to separate from the wall of the intestine or to pass easily from the subject's body. In an alternative embodiment, inner core 28 is removed from the body by being passed from the body, without a reduction in size. Thus, as appropriate, the inner core may be configured to (a) decrease in size in the small intestine, following drug delivery, (b) decrease in size in the colon, or (c) not decrease in size following drug delivery.

Figure 2:
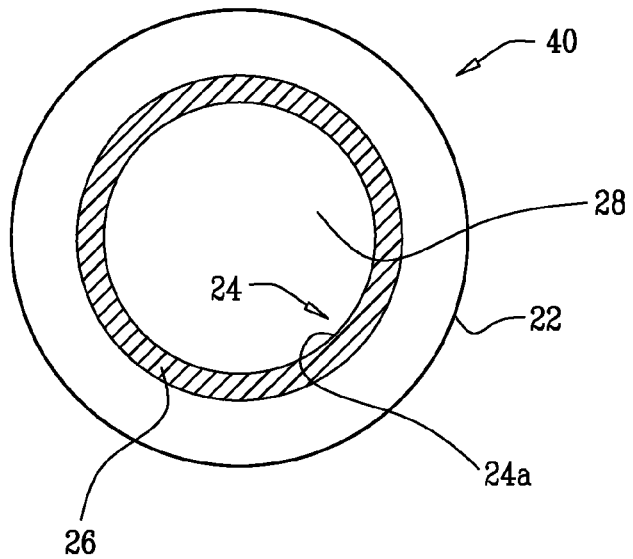
FIG. 2 is a schematic illustration of an ingestible expansible capsule, in accordance with an embodiment of the present invention.

Reference is now made to FIG. 2, which is a schematic illustration of a capsule 40, in accordance with an embodiment of the present invention. Capsule 40 is generally similar to capsule 20, as described hereinabove with reference to FIGS. 1A and 1B, except for differences as described hereinbelow.

In this embodiment, prior to expansion, outer surface 24a is generally circular in shape, although it is noted that the scope of the present invention includes a variety of initial shapes of the outer surface of the inner core. Following expansion, outer surface 24a is typically generally circular, due to it being pressed against intestinal wall 31. In some embodiments, medication 26 disposed on outer surface 24a of inner core 28 comprises a gel. In some embodiments, medication 26 is printed on outer surface 24a of inner core 28, using techniques known in the art. Medication 26 diffuses rapidly through the wall of the small intestine in response to the high concentration of medication 26 disposed on outer surface 24a, and the complete or nearly complete contact with the intestinal wall of expanded outer surface 24a of inner core 28.

Figure 3A:
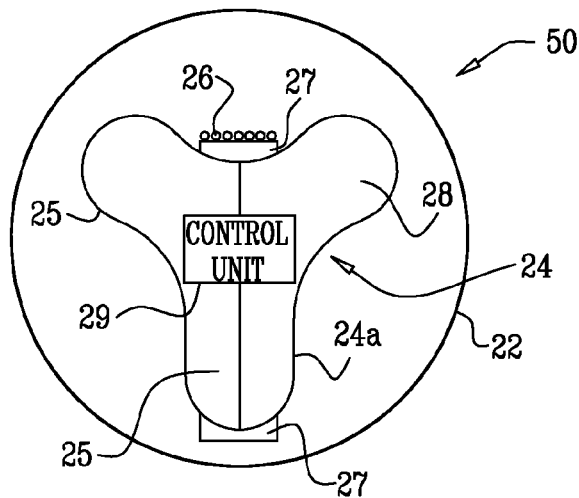
FIG. 3A and FIG. 3B are schematic illustrations of an ingestible expansible capsule, in accordance with respective embodiments of the present invention.
Figure 3B:
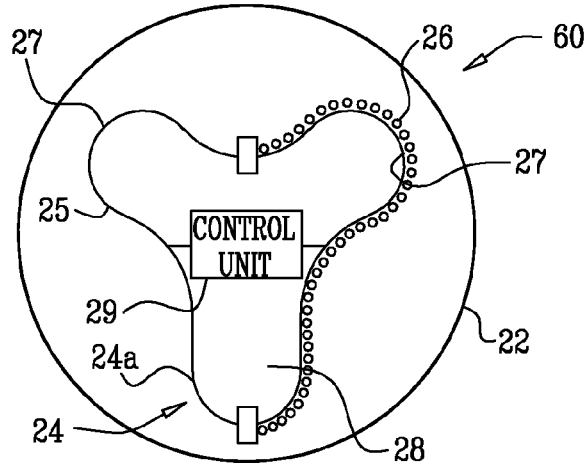

Reference is now made to FIG. 3A and FIG. 3B, which are schematic illustrations of a capsule 50 and a capsule 60, configured for ingestion by a subject, in accordance with respective embodiments of the present invention. Capsule 50 and capsule 60 are generally similar to capsules 20 and 40, as described hereinabove with reference to FIGS. 1A, 1B and 2, except for differences as described hereinbelow.

Inner core 28 of capsule 50 and capsule 60 comprises a control unit 29 disposed therein. In these embodiments, prior to expansion, outer surface 24a has a plurality of arms 25 extending radially outward toward coating 22 of capsules 50 and 60, although it is noted that the scope of the present invention includes a variety of initial shapes of the outer surface of the inner core.

Typically, outer surface 24a is coupled to at least two electrodes 27. In one embodiment, a plurality of electrodes 27 are disposed on outer surface 24a, as shown in FIG. 3A. In another embodiment, electrodes 27 constitute outer surface 24a of inner core 28, or a part thereof, as shown in FIG. 3B. For some applications, electrodes 27 comprise foil electrodes surrounding inner core 28, whereby the expansion of outer surface 24a constitutes the expansion of the foil electrodes.

Medication 26 is disposed on at least one of electrodes 27 (e.g., one of electrodes 27, as shown in FIGS. 3A and 3B). In some embodiments, medication 26 comprises a powder. In other embodiments, medication 26 comprises a gel. Outer surface 24a expands, establishing contact between the medication and the wall of the small intestine. Control unit 29, disposed within inner core 28, facilitates the delivery of medication 26 by driving a current through electrodes 27 into the intestinal wall. In one embodiment, control unit 29 iontophoretically drives medication 26 disposed on outer surface 24a through the intestinal wall. Alternatively or additionally, control unit 29 drives a current configured to increase the permeability of the intestinal wall to medication 26 (e.g., as described in US 2008/0063703 to Gross, which is incorporated herein by reference). In either case, techniques described in references cited in the Background section of the present patent application are typically adapted for use with these embodiments of the present invention, in order to facilitate passage of the medication through the intestinal wall.

Figure 4:
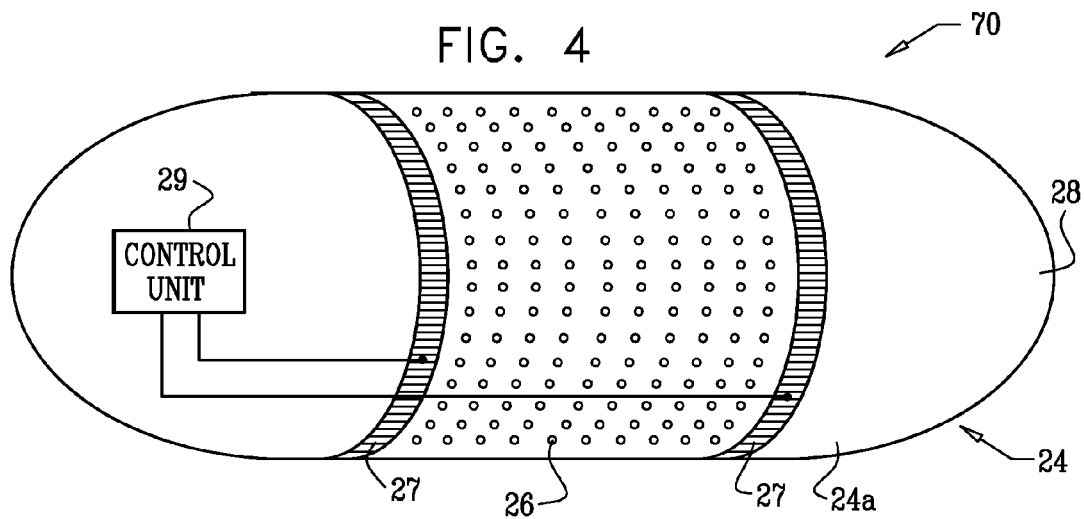
FIG. 4 is a schematic illustration of a portion of an ingestible capsule, in accordance with an embodiment of the present invention.

Reference is now made to FIG. 4, which is a schematic illustration of a capsule 70, after coating 22 has dissolved in the small intestine, in accordance with an embodiment of the present invention. Capsule 70 is generally similar to capsules 50 and 60, as described hereinabove with reference to FIGS. 3A and 3B, except for differences as described hereinbelow. Medication 26 is disposed on a portion of outer surface 24a, typically surrounded on either side by electrodes 27. In one embodiment, control unit 29 iontophoretically drives medication 26 through the intestinal wall. Alternatively or additionally, control unit 29 drives a current into the intestinal wall configured to increase the permeability of the intestinal wall to medication 26.

Although embodiments have been described with reference to capsules 50, 60 and 70, in which the capsule includes a control unit that facilitates the delivery of medication 26 by driving a current through electrodes and into the intestinal wall, the scope of the present invention includes applying these embodiments to any of the capsules described herein.

Additionally, although embodiments have been described in which a capsule is configured to deliver medication to the small intestine, the scope of the present invention includes using the methods and apparatus described herein to deliver medication to a subject's large intestine.

Figure 5A:
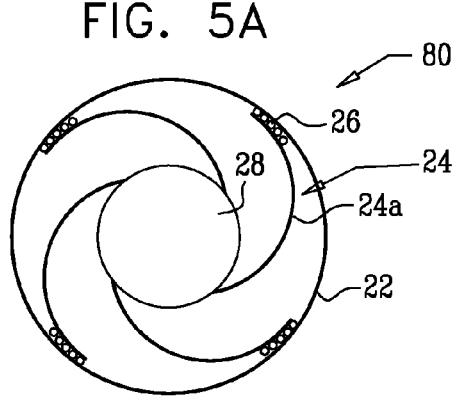
FIGS. 5A and 5B are schematic illustrations of an ingestible expansible capsule, in accordance with an embodiment of the present invention.
Figure 5B:
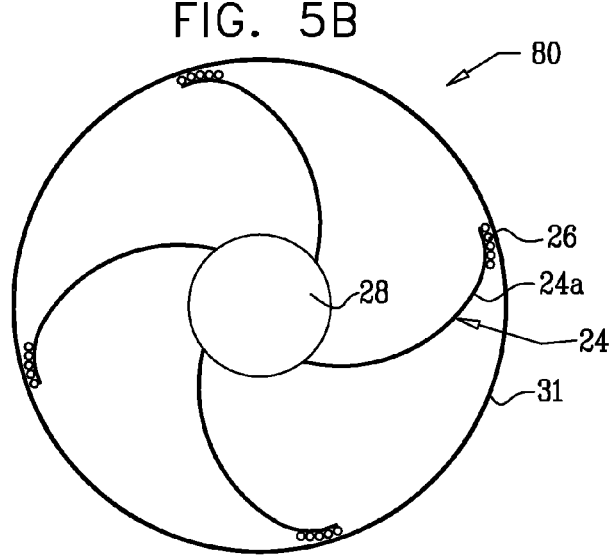

Reference is now made to FIGS. 5A and 5B, which are schematic illustrations of an ingestible capsule 80, in accordance with an embodiment of the present invention. Capsule 80 is generally similar to the capsules described hereinabove with reference to FIGS. 1-4, except for differences as described hereinbelow.

In some embodiments, outer surface 24a includes one or more flaps wrapped around inner core 28. Upon entering the subject's gastrointestinal tract (for example, small intestine 31), coating 22 dissolves and the flaps unroll (as shown in FIG. 5B). Typically, medication 26 is disposed on one or more of the flaps, and the flaps, when unrolled, bring the medication into contact with the wall of the gastrointestinal tract.

In some embodiments, a single flap is wrapped around inner core 28 in a scroll-like manner, i.e., in a manner similar to that of the flap described hereinbelow with reference to FIGS. 6A and 6B. Alternatively, a plurality of flaps are wrapped around inner core 28, as shown in FIGS. 5A and 5B.

Figure 6A:
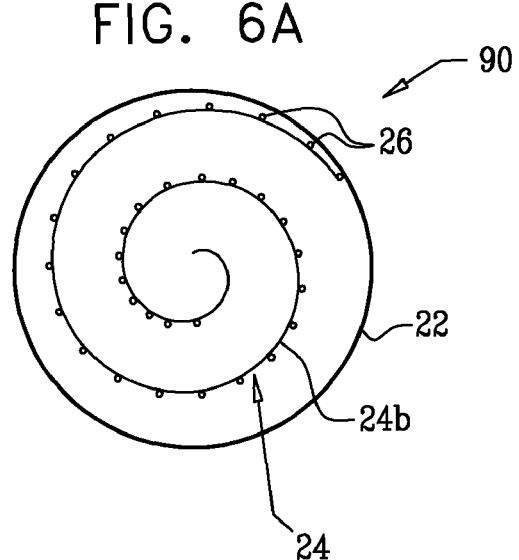
FIGS. 6A and 6B are schematic illustrations of an ingestible expansible capsule, in accordance with another embodiment of the present invention.
Figure 6B:
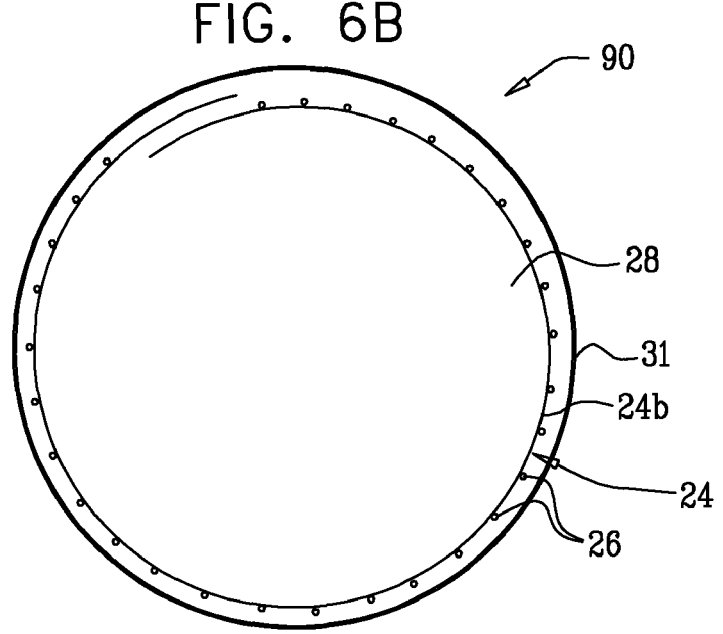

Reference is now made to FIGS. 6A and 6B, which are schematic illustrations of an ingestible capsule 90, in accordance with an embodiment of the present invention. Capsule 90 is generally similar to the capsules described hereinabove with reference to FIGS. 1-5, except for differences as described hereinbelow.

In some embodiments, capsule 90 comprises a surface 24b of a sheet (for example, a sheet of plastic or metal). In some embodiments, the sheet is rolled up in a scroll-like manner inside coating 22. Medication 26 is disposed on the surface. Upon entering the subject's gastrointestinal tract (for example, the subject's small intestine 31), coating 22 dissolves and surface 24b expands, bringing medication 26 into contact with the wall of the subject's gastrointestinal tract, for example the wall of the subject's small intestine 31, as shown in FIG. 6B.

Reference is now made to FIG. 7, which is a schematic illustration of a device 102 disposed inside an ingestible capsule 100, in accordance with an embodiment of the present invention. Capsule 100 is generally similar to the capsules described hereinabove with reference to FIGS. 1-6, except for differences as described hereinbelow.

In some embodiments, capsule 100 includes a surface 24c, medication 26 being disposed on the surface. Surface 24c is sized such that the medication contacts a wall of the subject's gastrointestinal tract (for example, the wall of small intestine 31) when the capsule is disposed within the subject's gastrointestinal tract. Typically, the surface defines a lateral diameter D thereof of at least 8 mm, typically 10 mm to 20 mm (for example, 12 mm to 15 mm), a length L of the capsule, perpendicular to the lateral diameter, being at least 8 mm. In some embodiments, lateral diameter D is 20 mm to 25 mm. Further typically, surface 24c is substantially non-expansible, lateral diameter D of the capsule when the capsule is swallowed by the subject being approximately equal to lateral diameter D when the capsule is disposed within the subject's gastrointestinal tract (excluding any change due to the dissolving of a coating). Still further typically, at least 80% of medication 26 is disposed within 1 mm of an outermost border of the capsule. In some embodiments, at least 90% of the medication is within an outer 1 mm of the radius of the capsule.

In some embodiments, surface 24c is sized such that it holds the surface in contact with the subject's intestine during delivery of medication 26 through the wall of the intestine. For some applications, an adhesive agent 116 transiently adheres the surface in position in the gastrointestinal tract during delivery of the medication through the wall of the gastrointestinal tract, as described hereinabove. For example, the adhesive agent may include an adhesive agent described in U.S. Pat. No. 6,235,313 to Mathiowitz et al., or in the above-cited article by Tao et al., both of which references are incorporated herein by reference.

In some embodiments, surface 24c and medication 26 are coated with coating 22. Typically, the coating dissolves in the subject's small intestine. Typically, upon dissolution of the coating, medication 26 is brought into contact with the wall of the intestine by surface 24c.

In some embodiments, device 102 is a sensor, and/or an imaging device that senses a parameter or images an image while the device is disposed within the subject's gastrointestinal tract. For example, device 102 may include an imaging device that includes a camera 112, a light source 110 (for lighting up the field-of-view of the camera) and/or a control unit 114. For some applications, device 102 includes a device that is generally similar to those described in U.S. Pat. No. 7,009,634 to Iddan, or in US Patent Application Publication 2006/0178557 to Mintchev et al., both of which references are incorporated by reference herein. In some embodiments, capsule 100 is sufficiently large that it contains therein a device that has a length L1 that is greater than 3 mm and a width W that is greater than 3 mm.

Reference is now made to FIG. 8, which is a schematic illustration of device 102 inside an ingestible capsule 120, in accordance with an embodiment of the present invention. Ingestible capsule 120 is generally similar to ingestible capsule 100 described hereinabove with reference to FIG. 7, except as described hereinbelow. In some embodiments, in response to a parameter detected by device 102, and/or in response to an image imaged by device 102, control unit 114 facilitates delivery of medication 26 through the intestinal wall. For example, in response to a parameter detected by device 102, and/or in response to an image imaged by device 102, and/or in response to a signal received from outside the patient's body, the control unit may drive a current into the intestinal wall, via electrodes 27, using techniques such as those techniques described hereinabove with reference to FIGS. 3-4.

Figure 9:
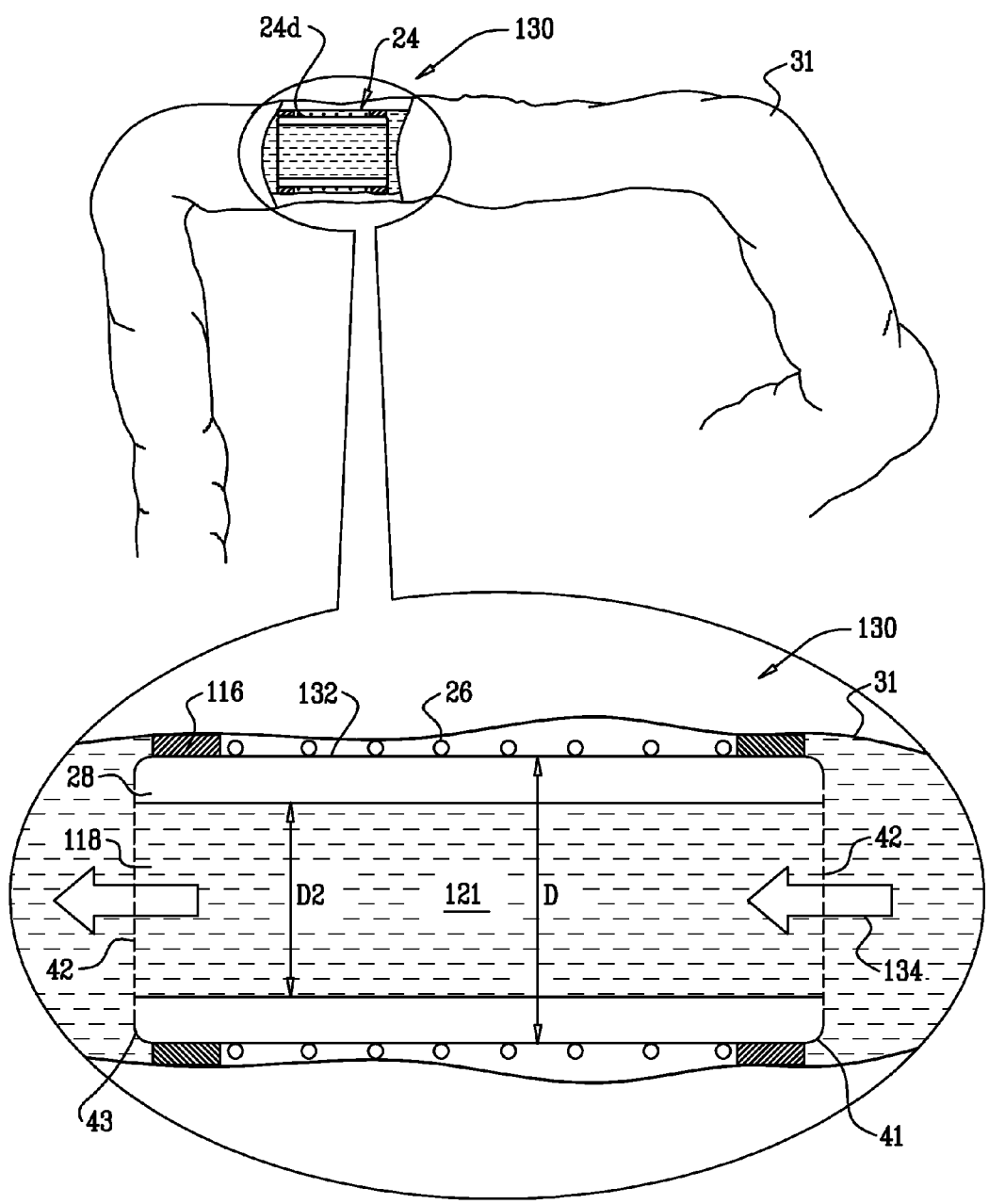
FIG. 9 is a schematic illustration of a capsule disposed within a subject's gastrointestinal tract, in accordance with an embodiment of the present invention.

Reference is now made to FIG. 9, which is a schematic illustration of a capsule 130 disposed within a subject's gastrointestinal tract, in accordance with an embodiment of the present invention. Capsule 130 is generally similar to the capsules described hereinabove with reference to FIGS. 1-8, except for differences as described hereinbelow.

A surface 24d of capsule 130 brings medication 26 into contact with a wall of the gastrointestinal tract (for example, a wall of small intestine 31). For some applications, capsule 130 is configured to allow gastrointestinal contents of the subject to pass through the capsule from proximal end 41 to distal end 43 of the capsule, when the capsule is disposed within the subject's gastrointestinal tract. (It is noted that the labels "distal end" and "proximal end" are used herein with respect to the end of the capsule which is oriented distally (away from the mouth) or proximally (toward the mouth), and is typically not predetermined as an inherent property of the capsule.) In some embodiments, capsule 130 is an expansible capsule, as described hereinabove. For example, surface 24d may be an expansible outer surface of an inner core, as described hereinabove. Alternatively, capsule 130 is a substantially non-expansible capsule, as described hereinabove. For example, surface 24d may be a substantially non-expansible surface.

In some embodiments, there are capsule end-surfaces 42 at proximal end 41 and distal end 43 of the capsule, and at least a portion of each of the capsule end-surfaces biodegrades when the capsule is disposed within the subject's gastrointestinal tract (for example, within the subject's small intestine 31), allowing gastrointestinal contents to pass through the capsule in the direction of arrow 134 (typically from proximal end 41 to distal end 43). In embodiments in which capsule 130 includes inner core 28, at least a portion 118 of the inner core also biodegrades when the capsule is disposed within the gastrointestinal tract, such that the inner core defines a lumen 121 therethrough. Alternatively or additionally, at least a portion 118 of the inner core is open, so as to define lumen 121 therethrough.

In some embodiments, at least a portion of each of proximal end 41 and distal end 43 is open, allowing gastrointestinal contents to pass through the capsule. The open portion of each of the ends of the capsule typically defines a diameter D2 that is 50%-90% of diameter D of the capsule. For example, capsule 130 may be substantially non-expansible and shaped as an open tube when swallowed by the subject. In embodiments in which the capsule includes inner core 28, at least a portion 118 of the inner core is open, and the subject's gastrointestinal contents flows therethrough from the proximal end to the distal end of the capsule.

In an embodiment, capsule 130, or any of the other capsules described herein, comprises a mucoadhesive, for example, adhesive agent 116, coupled to medication 26. The mucoadhesive and medication are to some extent rubbed off onto the inner wall of the gastrointestinal tract, and the mucoadhesive binds the drug to the inner wall, whereby diffusion of the medication through the epithelium and into the bloodstream is enhanced compared to if no adhesive were used, and the medication were to mix with the contents of the gastrointestinal tract. Many suitable mucoadhesive preparations are known in the art.

Figure 10:
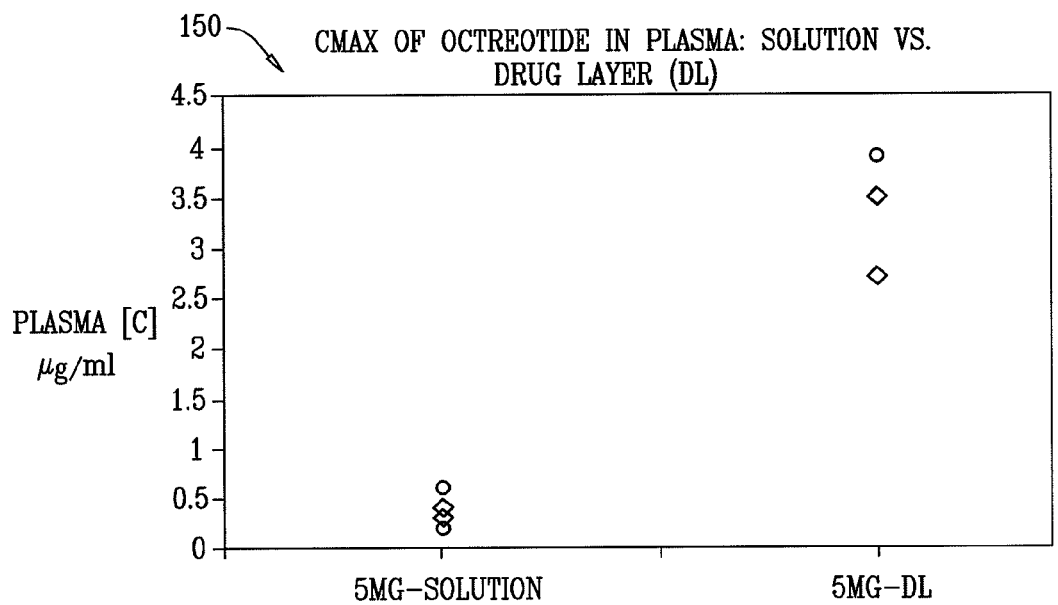
FIG. 10 is a graph illustrating the maximum plasma concentrations of octreotide measured in rats, resulting from administration of octreotide to the rats, in accordance with an embodiment of the present invention.

Reference is now made to FIG. 10, which is a graph 150 illustrating the maximum plasma concentration of octreotide measured in rats, resulting from administration of octreotide to the rats, in accordance with an embodiment of the present invention.

A control test was conducted on seven control rats. A 5 mg solution of octreotide was endoscopically administered to the control rats, and the resulting maximum plasma concentrations of octreotide in the control rats were measured. The maximum plasma concentrations measured in the control rats are shown below in the left column of Table 1. The maximum plasma concentrations measured in the control rats are plotted toward the left of graph 150.

TABLE 1

Maximum plasma octreotide measured in control and test rats

| Maximum concentration in control rats (µg/ml) | Maximum concentration in test rats (µg/ml) |
|---|---|
| 0.2 | 3.5 |
| 0.58 | 2.7 |
| 0.4 | 3.9 |
| 0.62 | |
| 0.28 | |
| 0.6 | |
| 0.3 | |

Octreotide was administered to three test rats using techniques that were in accordance with embodiments of the present invention. A drug layer of 5 mg of octreotide was dried onto the outer layer of each of three capsules, and the capsules were endoscopically placed in the small intestine of the three test rats. The resulting maximum plasma concentrations of octreotide in the test rats were measured. The maximum plasma concentrations measured in the test rats are shown in the right column of Table 1. The maximum plasma concentrations measured in the control rats are also plotted toward the right of graph 150. It is seen that for the same initial level of administered octreotide (5 mg), the resultant blood concentration of octreotide is significantly higher in (a) the test group, in which the capsule had 5 mg octreotide placed on the outer surface of the capsule, so as to be in direct contact with the wall of the gastrointestinal tract, than in (b) the control group, in which the 5 mg of octreotide was able to mix with gastrointestinal tract contents and not be entirely in direct contact with the wall of the gastrointestinal tract.

Figure 11:
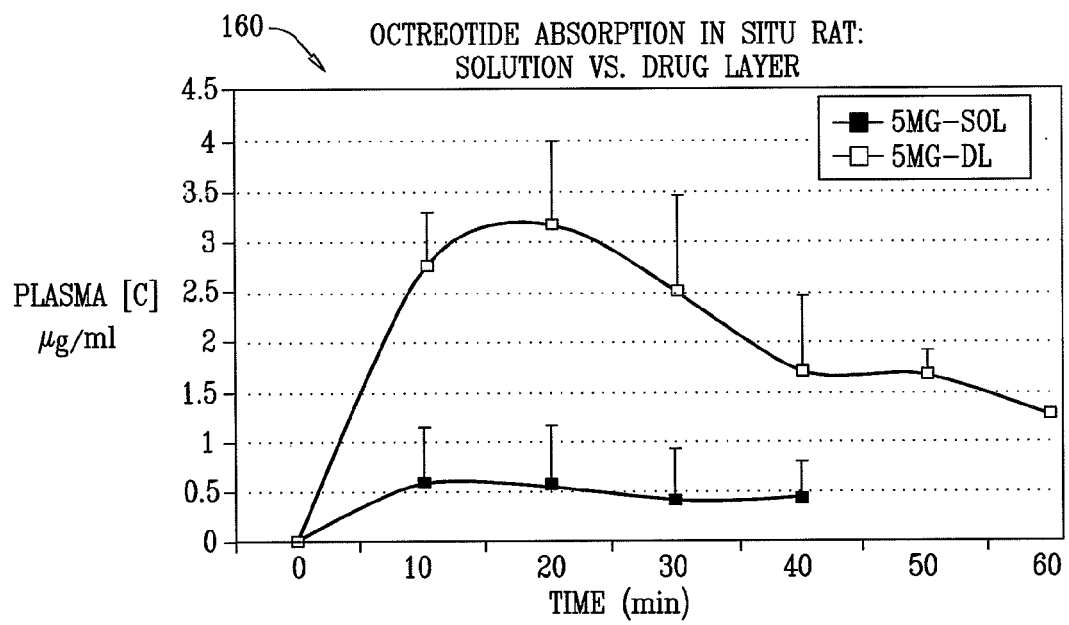
FIG. 11 is a graph illustrating the variation of plasma concentration of octreotide measured in rats, resulting from administration of octreotide to the rats, in accordance with an embodiment of the present invention.

Reference is now made to FIG. 11, which is a graph 160 illustrating the variation of plasma concentrations of octreotide in rats with time, resulting from administration of octreotide to the rats, in accordance with an embodiment of the present invention.

A control test was conducted on eight control rats, the control test being generally similar to the control test described above with reference to FIG. 10. Measurements were made of the mean plasma concentration of octreotide in the control rats with time, resulting from administration of octreotide to the control rats. The mean plasma octreotide concentration of the control rats is the lower curve plotted on graph 160.

Octreotide was administered to three test rats using techniques that were in accordance with embodiments of the present invention, and as described above with reference to FIG. 10. Measurements were made of the mean plasma concentration of octreotide in the test rats over time, resulting from administration of octreotide to the test rats. The results are shown as the top curve plotted on graph 160.

It may be observed that medication disposed at high concentration on a surface of a capsule results in a greater amount of the medication being absorbed than is absorbed if the medication is administered in solution. It is hypothesized by the inventor that this is because the capsule brings a high concentration of the medication disposed on the capsule's surface into contact with the wall of the subject's gastrointestinal tract.

For some applications, the techniques described herein are practiced in combination with techniques described in one or more of the following references, all of which references are incorporated herein by reference:

US Patent Application Publication 2004/0253304 to Gross et al.
US Patent Application Publication 2004/0267240 to Gross et al.
US Patent Application Publication 2005/0058701 to Gross et al.
US Patent Application Publication 2006/0276844 to Alon et al.
US Patent Application Publication 2008/0063703 to Gross et al.
US Patent Application Publication 2008/0275430 to Belsky et al.
US Patent Application Publication 2008/0188837 to Belsky et al.

For example, a driving mechanism for driving a drug through the gastrointestinal tract wall and/or for enhancing the permeability of the gastrointestinal tract wall to the drug, as described in one or more of the above references, may be used in combination with an expansible capsule, as described herein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An ingestible capsule for delivering medication to a subject, comprising:
    a coating configured to dissolve in a gastrointestinal tract of the subject;
    an inner core having an outer surface associated therewith, the outer surface being disposed within the coating and configured to expand when the coating dissolves; and
    a medication disposed on the outer surface, the outer surface being configured such that the medication contacts an intestinal wall of the subject when the outer surface expands,
    wherein the outer surface defines a lateral diameter thereof being at least 8 mm,
    wherein a length of the capsule, perpendicular to the lateral diameter, is at least 8 mm, and
    wherein at least 80% of the medication is within 1 mm of an outermost border of the capsule.

2. The capsule according to claim 1, further comprising an adhesive agent configured to adhere the medication to the subject's intestinal wall during delivery of the medication.

3. The capsule according to claim 1, wherein the medication comprises a powder.

4. The capsule according to claim 1, wherein the outer surface has a plurality of arms extending outward radially, prior to expansion.

5. The capsule according to claim 1, wherein the outer surface is configured such that on expansion of the outer surface, the medication disposed on the outer surface contacts the intestinal wall providing 360 degrees of contact of the medication with the intestinal wall.

6. The capsule according to claim 1, wherein the coating comprises a gelatin coating configured to constrain the outer surface from expanding before the gelatin coating dissolves.

7. The capsule according to claim 1, wherein a diameter of the inner core after expansion is between 10 mm and 14 mm.

8. The capsule according to claim 1, wherein the outer surface is configured to facilitate delivery of the medication through the intestinal wall by establishing the contact between the medication and the intestinal wall, further comprising an adhesive agent configured to hold the outer surface in position during the delivery of the medication through the intestinal wall.

9. The capsule according to claim 1, further comprising a control unit and two electrodes, wherein the control unit is configured to facilitate delivery of the medication through the intestinal wall by driving a current through the electrodes.

10. The capsule according to claim 1, wherein the outer surface is configured to be separated at least in part from the inner core during the expansion of the outer surface.

11. The capsule according to claim 10, wherein the outer surface comprises one or more flaps wrapped around the inner core prior to expansion, which are configured to separate from the inner core by unrolling from the inner core.

12. The capsule according to claim 1, wherein the capsule is configured to allow gastrointestinal contents of the subject to pass through the capsule, from one end of the capsule to another end of the capsule, when the capsule is disposed within the subject's gastrointestinal tract and subsequent to expansion.

13. An ingestible capsule for delivering medication to a subject, comprising:
    a surface, defining a lateral diameter thereof being at least 8 mm,
        a length of the capsule, perpendicular to the lateral diameter, being at least 8 mm; and
    a medication disposed on the surface, at least 80% of the medication being within 1 mm of an outermost border of the capsule.

14. The capsule according to claim 13, wherein at least 90% of the medication is within an outer 1 mm of the radius of the capsule.

15. The capsule according to claim 13, further comprising a medication-layer disposed on the surface, the medication-layer comprising more than 90% by volume of the medication.

16. The capsule according to claim 13, wherein the lateral diameter is 10 mm to 20 mm.

17. The capsule according to claim 13, further comprising a control unit and two electrodes, wherein the control unit is configured to facilitate delivery of the medication through an intestinal wall by driving a current through the electrodes, and configuring the current to increase permeability of the intestinal wall to the medication.

18. The capsule according to claim 13, wherein the lateral diameter is 20 mm to 25 mm.

19. The capsule according to claim 13, wherein the surface is sized such that it holds the surface in position in a gastrointestinal tract of the subject during delivery of the medication through a wall of an intestine of the subject.

20. The capsule according to claim 13, further comprising an adhesive agent configured to adhere the medication to a wall of an intestine of the subject during delivery of the medication.

21. The capsule according to claim 13, further comprising an adhesive agent configured to adhere the surface in position during delivery of the medication.

22. The capsule according to claim 16, wherein the lateral diameter is 12 mm to 15 mm.

23. The capsule according to claim 13, further comprising a chemical enhancer configured to enhance delivery of the medication to the subject.

24. The capsule according to claim 23, wherein the chemical enhancer comprises lipophilic molecules configured to enhance diffusion of the medication through an epithelial layer of a gastrointestinal tract of the subject.

25. The capsule according to claim 13, further comprising a control unit and two electrodes, wherein the control unit is configured to facilitate delivery of the medication by driving a current through the electrodes.

26. The capsule according to claim 25, wherein the control unit is configured to facilitate delivery of the medication by iontophoretically driving the medication.

* * * * *